United States Patent
Assmann et al.

(10) Patent No.: US 7,145,334 B2
(45) Date of Patent: Dec. 5, 2006

(54) METHOD AND MAGNETIC RESONANCE TOMOGRAPHY APPARATUS FOR PRODUCING PHASE-CODED FLOW IMAGES

(75) Inventors: Stefan Assmann, Erlangen (DE); Martin Requardt, Nürnberg (DE); Ingo Schmitjans, Minden (DE); Oliver Schreck, Bamberg (DE)

(73) Assignee: Siemens Aktiengesellschaft, Munich (DE)

( * ) Notice: Subject to any disclaimer, the term of this patent is extended or adjusted under 35 U.S.C. 154(b) by 49 days.

(21) Appl. No.: 10/997,706

(22) Filed: Nov. 24, 2004

(65) Prior Publication Data

US 2005/0156593 A1    Jul. 21, 2005

(30) Foreign Application Priority Data

Nov. 28, 2003  (DE)  ............... 103 56 275

(51) Int. Cl.
    *G01V 3/00*   (2006.01)

(52) U.S. Cl. .................... 324/306; 324/307
(58) Field of Classification Search ........... 324/306, 324/307, 309
    See application file for complete search history.

(56) References Cited

U.S. PATENT DOCUMENTS

| 5,187,658 | A | * | 2/1993 | Cline et al. ........ 382/128 |
| 5,204,625 | A | * | 4/1993 | Cline et al. ........ 324/306 |
| 6,556,856 | B1 | * | 4/2003 | Mistretta et al. ...... 600/420 |

* cited by examiner

*Primary Examiner*—Louis M. Arana
(74) *Attorney, Agent, or Firm*—Schiff Hardin LLP

(57) ABSTRACT

In a method and MR apparatus for the automatic segmentation of flow images acquired by magnetic resonance tomography for the depiction of tissue or organs traversed with fluid such as blood, at least one phase image of a selected region of the subject is acquired by magnetic resonance tomography, and fluid-traversed regions in the at least one phase image are automatically segmented.

28 Claims, 5 Drawing Sheets

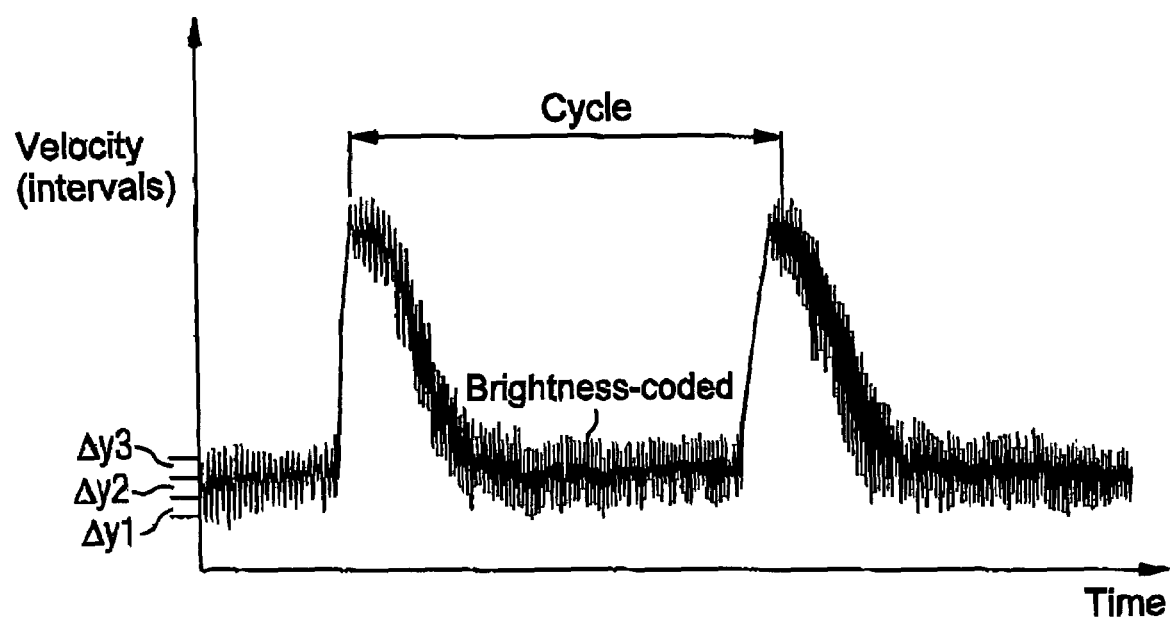

METHOD AND MAGNETIC RESONANCE TOMOGRAPHY APPARATUS FOR PRODUCING PHASE-CODED FLOW IMAGES

BACKGROUND OF THE INVENTION

1. Field of the Invention

The present invention concerns in general magnetic resonance tomography (MRT) as used in medicine for examination of patients. In particular, the invention concerns a method for the automatic segmentation of flow images acquired in magnetic resonance tomography for the depiction of, for example, arterial systems traversed (flowed through) with blood.

2. Description of the Prior Art

MRT is based upon the physical phenomenon of nuclear magnetic resonance and has been successfully used as an imaging modality in medicine and biophysics for over 15 years. The subject is exposed to a strong, constant magnetic field, cause the nuclear spins of the atoms in the subject, which were oriented randomly, to align. Radio-frequency energy can now excite these "ordered" nuclear spins to a specific oscillation. This oscillation generates the actual measurement signal in MRT, which is acquired by means of suitable reception coils. The measurement subject can be spatially coded in all three dimensions, generally designated as spatial coding, by the use of non-homogeneous magnetic fields generated by gradient coils.

The acquisition of data in MRT ensues in k-space (frequency domain). The MRT image in the image domain is linked with the MRT data in k-space by Fourier transformation. The spatial coding of the subject, which spans k-space, ensues in all three directions by magnetic gradients, including a slice selection gradient (establishes a slice selection of the subject, typically the z-axis), a frequency-coding gradient (establishes a direction in the slice, typically the x-axis) and a phase coding gradient (determines the second dimension within the slice, typically the y-axis). Moreover, the selected slice can be sub-divided into further slices along the z-axis by phase coding.

Thus a slice is selectively excited, for example, in the z-direction, and a phase coding in the z-direction is simultaneously executed. The coding of the spatial information in the slice ensues via a combined phase and frequency coding, by means of both of these aforementioned orthogonal gradient fields which, in the example of a slice excited in the z-direction, are generated in the x-direction and y-direction by receptive already-cited gradient coils.

A possible form of a sequence for data acquisition in an MRT scan is depicted in FIGS. 6A and 6B. The sequence used is a spin-echo sequence. In this, the magnetization of the spins In the x-y plane is achieved by a 90°-excitation pulse. In the course of time (½ $T_e$; $T_e$ is the echo time), it leads to a dephasing of the magnetic components which together form the transverse magnetization in the x-y plane $M_{xy}$. After a certain time (for example, ½ $T_e$), a 180° pulse is emitted into the x-y plane, so that the dephased magnetization components are mirrored without changing the precession direction and precession velocity of the individual magnetization portions. After a further duration ½ $T_E$, the magnetization components again appear in the same direction, i.e. a regeneration of the transverse magnetization occurs, designated as a "rephasing. The complete regeneration of the transverse magnetization is designated as a spin-echo.

In order to acquire data for an entire slice of the subject to be examined, the imaging sequence is repeated N times with different values of the phase coding gradient, for instance $G^y$. The temporal separation of the respectively excited RF pulses is designated as the repetition time TR. The magnetic resonance signal (spin-echo signal) is likewise sampled, digitized, and stored N times in every sequence repetition by means of $\Delta t$-clocked ADC (analog-digital converter) in equidistant time steps in the presence of the read-out gradient $G^x$. In this manner (according to FIG. 6b) a numerical matrix is created row-by-row (matrix in k-space, or k-matrix) with N×N data points. An MR image of the slice inquisition can be directly reconstructed with a resolution of N×N pixels from this data set via a Fourier transformation (a symmetric matrix with N×N points is only one example, asymmetrical matrices can be generated as well).

For example, the curve of the average velocity of the flowing medium in a specified vessel during a movement cycle (breathing, heart movement) can be determined by velocity-resolved flow measurements in MRT, or the velocity distribution can be determined in a cross-section of the traversed vessel area of interest, or even further characteristic flow magnitudes at a specific point in time of the movement. For example, the velocity curve of the blood in the aorta during a heart cycle (from systole to systole) is of great interest.

For such measurements, two data sets are acquired virtually simultaneously during the movement, i.e. within a cycle to be measured: an anatomical image series as well as a velocity-coded image series. Typically the image acquisition rate in both series is approximately 20 images per cycle. The simultaneity of the image acquisition is realized by alternatingly acquiring an image of the one series followed by an image of the other series. During the acquisition of the velocity-coded series a constant gradient is applied in the flow direction that is adapted to the diverse sequence parameters (repetition time, flip angle, etc.) as well as to the flow velocity in the vessel of concern, in order to achieve an optimal velocity resolution. The acquisition slice of both series typically is oriented perpendicularly to the vessels to be depicted. The additional (phase coding) gradient in the flow direction is therefore necessary in order to be able to associate a defined velocity with every voxel of the flowing medium based upon the velocity-dependent dephasing, represented by the intensity of the magnetic resonance signal.

Conventionally the velocity-coded image series has been depicted in the form of a phase-coded flow image series and evaluated together with the anatomical image series with aid of post-processing software, generally after the completion of the examination on the patient. A quantified flow measurement is thereby possible by means of MRT, but as of yet there is no automatic evaluation and instantly surveyable depiction as is available, for example, in ultrasonic imaging. In the prior art, the user can separately view the flow image series (phase-coded image series) as well as the anatomical image series and optionally colorize the phase-coded image data set with non-standardized color palettes with the help of the post-processing software. The user can subsequently mark a flow region in both image series with a contour (border or outline), whereupon characteristic flow quantities of these marked areas are calculated and graphically presented.

The drawing of the contour can only ensue manually with a mouse. The evaluation of the marked areas must also be started manually. Moreover, a depiction of the velocity distribution in the form of a histogram—as is for instance standard with a Doppler ultrasonic examination—is presently not possible.

SUMMARY OF THE INVENTION

An object of the present invention is to provide a method allowing automatic recognition of the traversed regions in the available image series for flow measurements in MRT, and allowing automatic evaluation of the traversed regions and visualization thereof in a user-friendly manner.

This object is achieved according to the present invention by a method for automatic segmentation of fluid-traversed regions in a subject to be examined, including measurement of at least one phase image of a selected region of the subject by magnetic resonance tomography, and automatic segmenting of the traversed regions in the at least one phase image.

In a first embodiment of the inventive method, the automatic segmenting ensues by, for each pixel, retaining the pixel or deleting the pixel based on a brightness value comparison of that pixel in the at least one phase image with its neighbor pixel.

A defined number of neighbor pixels is typically considered.

However, it may be advantageous for the considered number of neighbor pixels should to be independent of the surroundings and to be established by the image computer based on an algorithm.

Neighbor pixels are considered along at least one of the eight primary directions.

The pixel in question is inventively retained or deleted given a brightness value difference dependent on a defined threshold value.

Where possible, in a further step of the segmenting it is advantageous also to implement a filtering dependent on the average value of the environment of each pixel.

In a further embodiment of the inventive method, at least one magnitude image is calculated based on the at least one phase image, and the segmentation of the traversed regions is implemented in the phase image using the at least one magnitude image.

The segmentation of the traversed regions advantageously ensues using a magnitude image segmenting algorithm that determines whether the appertaining pixel is retained or deleted based on a brightness value comparison of each pixel in the at least one magnitude image with a threshold value.

The deletion of the pixel can inventively ensue in the magnitude image or in the phase image.

It can be of advantage to implement the brightness value comparison with the average value of a neighborhood of each pixel.

The threshold value of the magnitude image-segmenting algorithm is advantageously selectable.

The threshold value also can be established based on evaluation of a histogram.

In a further embodiment of the inventive method, at least one anatomical image is acquired virtually simultaneously with the measurement of the at least one phase image, and a segmentation of the phase image is implemented using the at least one anatomical image.

This further segmentation ensues via an algorithm that, in the at least one anatomical image (possibly also in the at least one phase image and/or in the at least one magnitude image) for each traversed region, locates and samples at least one pixel inside the respective region at the border of the respective region.

The sampling is advantageously based on a method of border detection and/or edge detection.

In the inventive method, it is possible that three image types will have been segmented that respectively exhibit different segment quality. A confidence weighting is inventively used for evaluation of the segmentation of the same regions of the different three image types—phase image, magnitude image and anatomical image.

After segmentation has ensued, the segmented, blood-traversed regions can inventively undergo a subject analysis. The subject analysis concerns, among other things, the extent and area, the shape and size, the focal point, etc.

In the case of acquired image series, the segmented, traversed regions are inventively used as output regions for known contour adaptation algorithms or contour tracking algorithms applied over the respective image series.

A series-specific histogram associated with the respective region can likewise be inventively created for an acquired image series based on the determined velocity profile of the traversed regions.

The above object also is achieved by a magnetic resonance tomography apparatus that is suitable for implementation of the method described above.

The above object also is achieved by a computer software product implements a method according to the above when it runs in a computer connected with a magnetic resonance tomography apparatus.

DESCRIPTION OF THE DRAWINGS

FIG. 5 shows a histogram according to an ultrasound standard for illustration of the velocity distribution of the blood flow in the aorta during a heart cycle.

DESCRIPTION OF THE PREFERRED EMBODIMENTS

Figure 1:
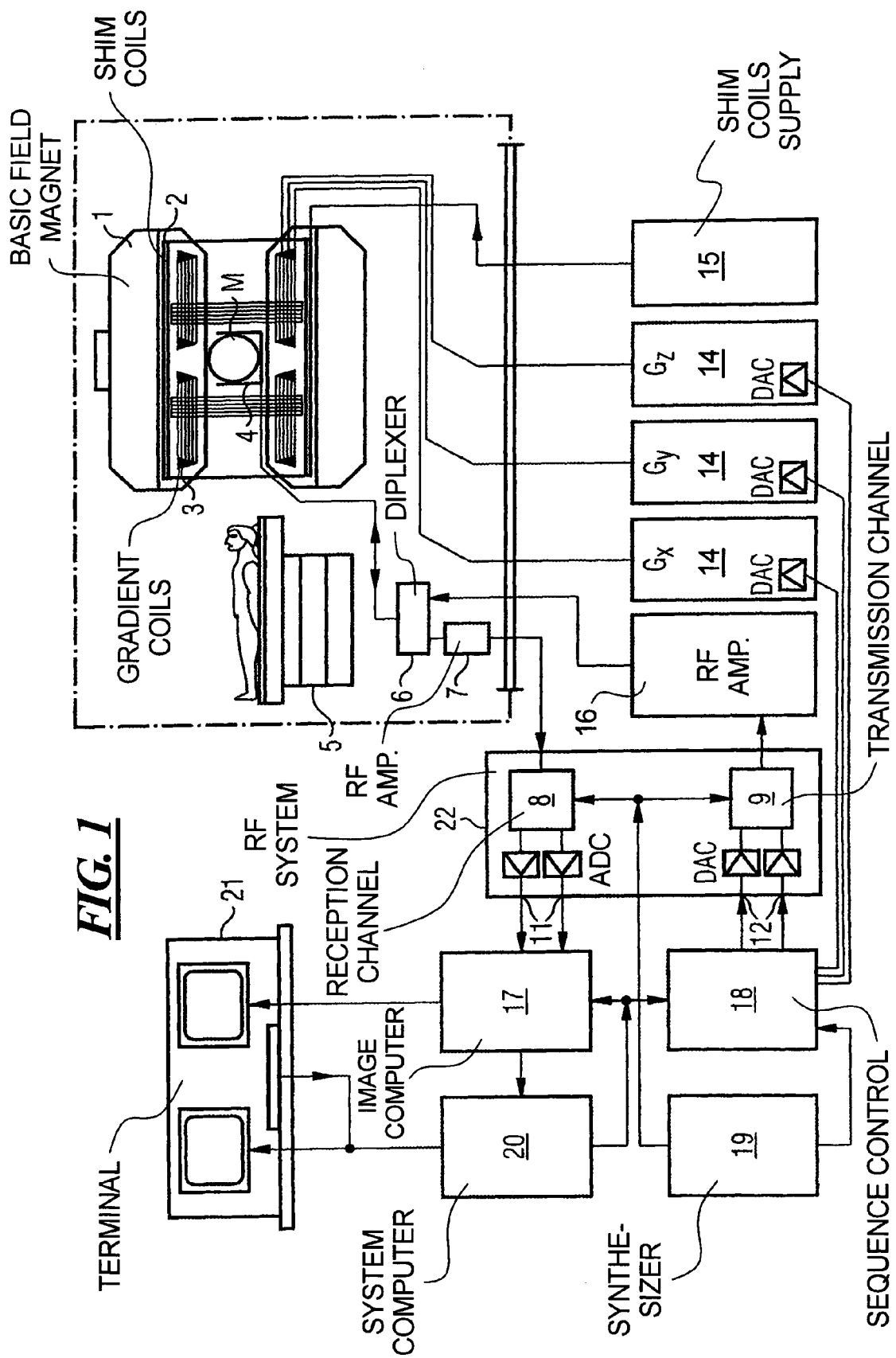
FIG. 1 schematically shows a magnetic resonance tomography apparatus for implementing the inventive method.

FIG. 1 is a schematic representation of a magnetic resonance tomography apparatus according to the present invention, with which optimized flow measurements are possible. The basic design of the magnetic resonance tomography apparatus corresponds to that of a conventional tomography apparatus, with the differences described below. A basic field magnet 1 generates a temporally constant strong magnetic field for polarization or alignment of the nuclear spins in the examination region of a subject such as, for example, a part of a human body to be examined. The high homogeneity of the basic field magnet necessary for the magnetic resonance measurement is defined in a spherical measurement volume M in which the parts of the human body to be examined are introduced. To support the homogeneity requirements, and in particular to eliminate temporally Invariable influences, shim plates made of ferromagnetic material are mounted at suitable locations. Temporally variable influences are eliminated by shim coils 2 that are activated by a shim current supply 15.

A cylindrical gradient coil system 3 that includes three windings is used in the basic field magnet 1. Each winding is supplied by an amplifier 14 with current to generate linear gradient field in respective directions of a Cartesian coordinate system. The first winding of the gradient field system 3 generates a gradient $G_x$ in the x-direction, the second winding of the gradient field system 3 generates a gradient $G_y$ in the y-direction, and the third winding of the gradient field, system 3 generates a gradient $G_z$ in the z-direction. Each amplifier 14 has a digital-analog converter that is controlled by a sequence controller 18 for time-accurate generation of gradient pulses.

Within the gradient field system 3 is a radio-frequency antenna 4 that transduces the radio-frequency pulse emitted by a radio-frequency power intensifier 30 into a magnetic alternating field to excite the aligned nuclei of the subject to be examined, or of the region of the subject to be examined. The alternating field originating from the precessing nuclear spins. generally the nuclear spin echo signals ensuing from a pulse sequence composed of one or more radio-frequency pulses and one or more gradient pulses, is also transduced by the radio-frequency antenna 4 into a voltage that is supplied via an amplifier 7 to a radio-frequency reception channel 8 of a radio-frequency system 22. The radio-frequency system 22 also has a transmission channel 9 in which the radio-frequency pulses are generated for the excitation of the magnetic nuclear resonance. The respective radio-frequency pulses are digitally represented in the sequence controller 18 as a sequence of complex numbers based on a pulse sequence predetermined by the system computer 20. This numerical sequence is supplied via respective inputs 12 as a real part and an imaginary part to a digital-analog converter in the radio-frequency system 22, and is supplied from this to the transmission channel 9. In the transmission channel 9, the pulse sequences are modulated by a radio-frequency carrier signal having a base frequency corresponding to the resonance frequency of the nuclear spins in the measurement volume.

The changeover from transmission mode to reception mode ensues via a transmission-reception diplexer 6. The radio-frequency antenna 4 radiates the radio-frequency pulses to excite the nuclear spins in the measurement volume M and samples resulting echo signals. The correspondingly acquired magnetic resonance signals are phase-sensitively demodulated in the reception channel 8 of the radio-frequency system 22 and converted via respective digital-analog converters into a real part and an imaginary part of the measurement signal. An image is reconstructed by an image computer 17 from the measurement data acquired in such a manner. The administration of the measurement data, the image data and the control program ensues via the system computer 20. Based on a specification with control programs, the sequence controller 18 monitors the generation of the desired pulse sequences and the corresponding scanning of k-space. In particular, the sequence controller 18 controls the time-accurate switching of the gradients, the emission of the radio-frequency pulses with defined phase and amplitude, and the reception of the magnetic resonance signals. The time base for the radio-frequency system 22 and the sequence controller 18 is provided by a synthesizer 19. The selection of corresponding control programs to generate a magnetic resonance image, as well as the representation of the generated magnetic resonance image, ensues via a terminal 21 that has a keyboard as well as one or more screens.

The described MRT apparatus includes a computer or image processing unit (for example in the system computer 20) which, according to the inventive method, automatically recognizes, evaluates and graphically displays (for example in ultrasound color Doppler representation or in the form of a histogram according to the present ultrasound standard) at the terminal 21 the fluid-traversed regions in the underlying images containing anatomical information as well as flow or velocity information.

As described above, in MRT flow measurements velocity-coded series and anatomical image series are typically acquired virtually simultaneously, preferably over a movement cycle of interest. The velocity-coded images generally also contain velocity information in the traversed regions. The traversed regions are also normally well recognized in the anatomical images; but no specific flow parameters can be derived from them.

The present invention allows the fluid-traversed regions to be segmented based on calculations, thus automatically, in order to subsequently effect a likewise automatic evaluation and corresponding visualization of the results. A segmentation ensues either for each individual image of an image series or the automatically segmented traversed regions of an image are used as starting regions for known contour tracking algorithms applied over the respective image series.

For simplification and in the context of an explanation of the inventive method, the automated segmenting of only one image of an acquired image series is considered. Typically, two different measurements are initially implemented virtually simultaneously. One measurement provides a velocity-compensated image and the other measurement provides a velocity-coded image. In the velocity-compensated image—also called an "anatomical image"—the fact that the signal sources (precessing nuclei) exhibit velocities does not provide a signal contribution. Every measurement value is characterized by a vector of definite length and definite direction in the complex plane. The measurement values of a velocity-coded image likewise represent complex vectors, with the coding of velocity manifested as a phase shift of the respective vector relative to the corresponding vector of the anatomical image. By formation of the magnitude difference of the corresponding vectors of both images, an image known as a magnitude image can be obtained in which the velocity is coded directionally independent, with the blood-traversed regions exhibiting higher brightness. By formation of the phase difference of the corresponding vectors of both images, an image is known as a phase image can be obtained in which velocity is coded directionally dependent. In the phase image the traversed regions with velocities in one direction exhibit higher brightness regions, and velocities in the opposite direction exhibit lesser brightness, than the immediate static surroundings. In this manner, three image types that can be used for automatic segmentation of fluid traversed regions are available to the user.

Figure 2A:
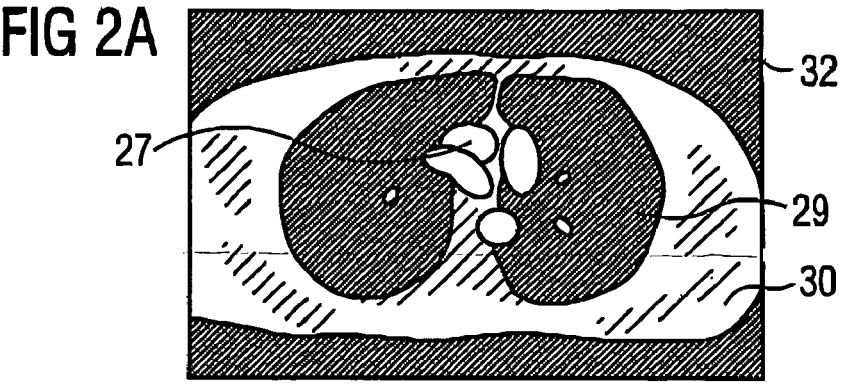
FIG. 2A shows an image from the anatomical image series (anatomical image) in the form of a blood transversal cross-section of the aorta in the mediastinum.
Figure 2B:
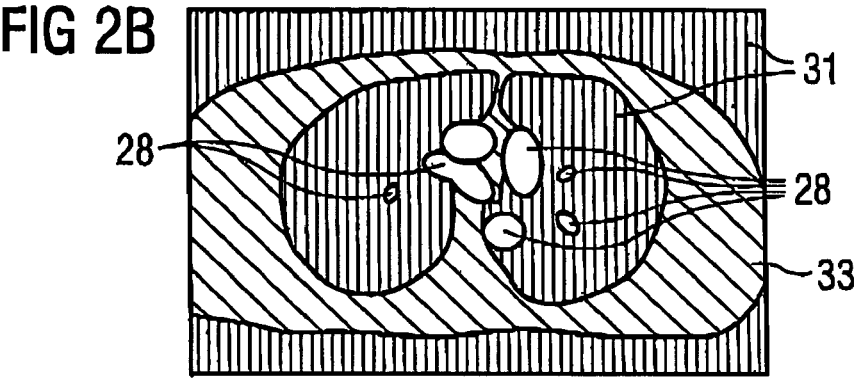
FIG. 2B shows an image from the phase-coded image series (phase image) of the same cross-section as in FIG. 2A.
Figure 2C:
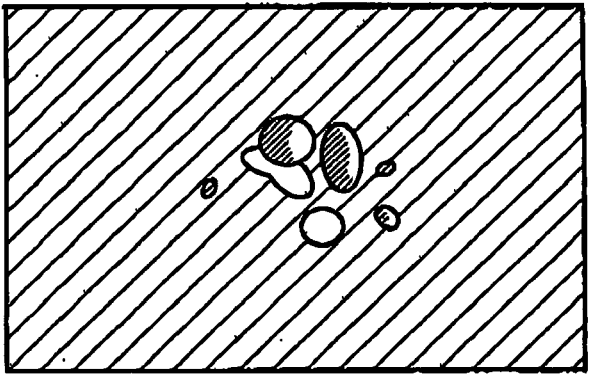
FIG. 2C shows an image from the magnitude image series (magnitude image) of the same cross-section as in FIG. 2A

The three image types are represented in FIGS. 2A, 2B and 2C. FIG. 2A shows an image from the anatomical image series—designated as an anatomical image in the following—in the form a transversal cross-section of the aorta 27 in the mediastinum of a patient to be examined. Both lobes

29 of the lung as well as the region outside of the patient 32 are shown in black. Further blood-traversed tissue (as an example of a fluid-traversed region 28 as well as their vessel walls in the region of the aorta 27 are recognizable as bright, closed structures.

FIG. 2B shows a phase image in which the velocity information is quantitatively contained in the non-hatched regions 28, 29. The hatched regions 31, 33 show statistical noise, with the pixel values of the noise in the air-filled, lengthwise-hatched region 31 extend across the entire value range (from white across grey to black), which is also designated as black-and-white noise, and the static anatomical tissue (crosswise hatching 33) is superimposed by lesser static noise.

FIG. 2C shows a magnitude image which exclusively shows the flow areas, while the remaining region (crosswise-hatched) us characterized by a uniform grey value (this means that no visible structure is detectable). As already mentioned, the magnitude image is obtained by formation of the magnitude difference of the corresponding vectors from velocity-coded and velocity-compensated images. The flow areas are represented as closed regions that likewise contain velocity information, but give no information about the direction of the flow.

This is due to the fact that two velocity values with opposite signals are associated with a magnitude value.

Figure 2D:
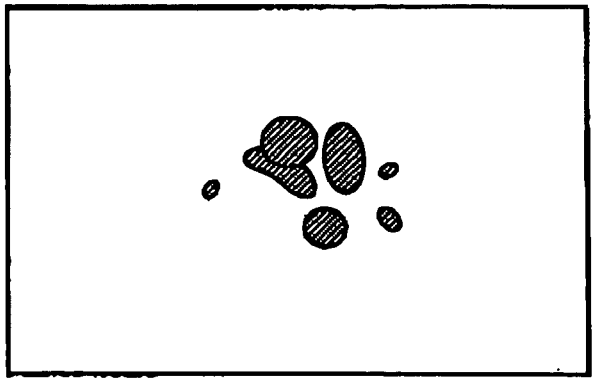
FIG. 2D shows a mask image in the form of a black-and-white mask which exclusively shows blood-traversed regions.

In a black-and-white mask, FIG. 2D ultimately, purely qualitatively shows the blood-traversed regions in contrast to the velocity-coded images (phase image and magnitude image) in which the voxels of higher velocity are represented as regions of higher or lower brightness.

This effect is based on what is known as the "phase contrast method", in which two opposite gradients of exactly the same magnitude are switched in the flow direction in the temporal interval. In the case of static, spin-resonant matter, the spins under the influence of the first gradient experience a dephasing that is completely cancelled again under the influence of the second inverted gradient. In the contrast agent enrichment of moving (flowing), spin-resonant matter, no complete rephasing ensues because the spins are located at different locations at the time during which the second gradient is switched and—considered over time—do not experience the same rephasing that caused them to be dephased. A phase difference remains that is proportional to the velocity of the flowing matter. The faster a spin-resonant particle moves through the (flow) gradient field, the stronger it is ultimately dephased from the null position.

FIGS. 2A, 2B, 2C and 2D show, the phase image (FIG. 2B) alone possesses the complete quantitative and direction-resolved velocity information of the traversed regions.

For this reason, in the inventive method initially an automatic segmenting of the traversed region is implemented in the phase image. One possibility for the automatic segmentation exists, for example, in the implementation of a neighborhood analysis, by the output pixel being retained or deleted based on a brightness value comparison of each pixel of the phase image with its neighbor pixels. The number of the neighbor pixels to be considered can be defined by the user or be established by the computer dependent on the surroundings.

Figure 3:
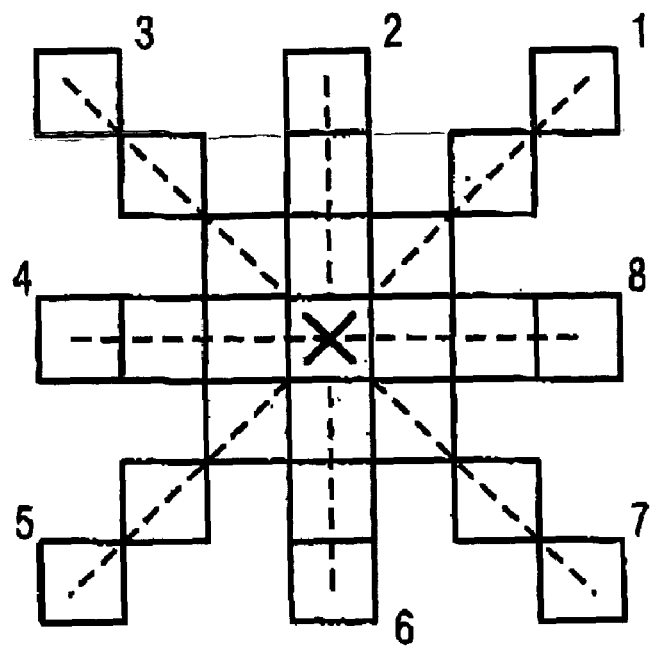
FIG. 3 illustrates a neighborhood analysis along the eight primary directions under consideration of three neighbor pixels.

The consideration of the neighbor pixel ensues along at least one of the eight primary directions, as shown, for example, in FIG. 3. In the example of FIG. 3, the brightness values of three neighbor pixels are considered and, given an occurring brightness value difference above a threshold, the output pixel is deleted. The contiguous areas of the phase image are obtained with this filtering, and the large fluctuations of the (black-and-white) noise are filtered from these. A weak noise remains in the image, however, which is why a filtering with regard to the average value of the surroundings of each pixel must be implemented in a second step of the automatic segmentation.

Figure 4:
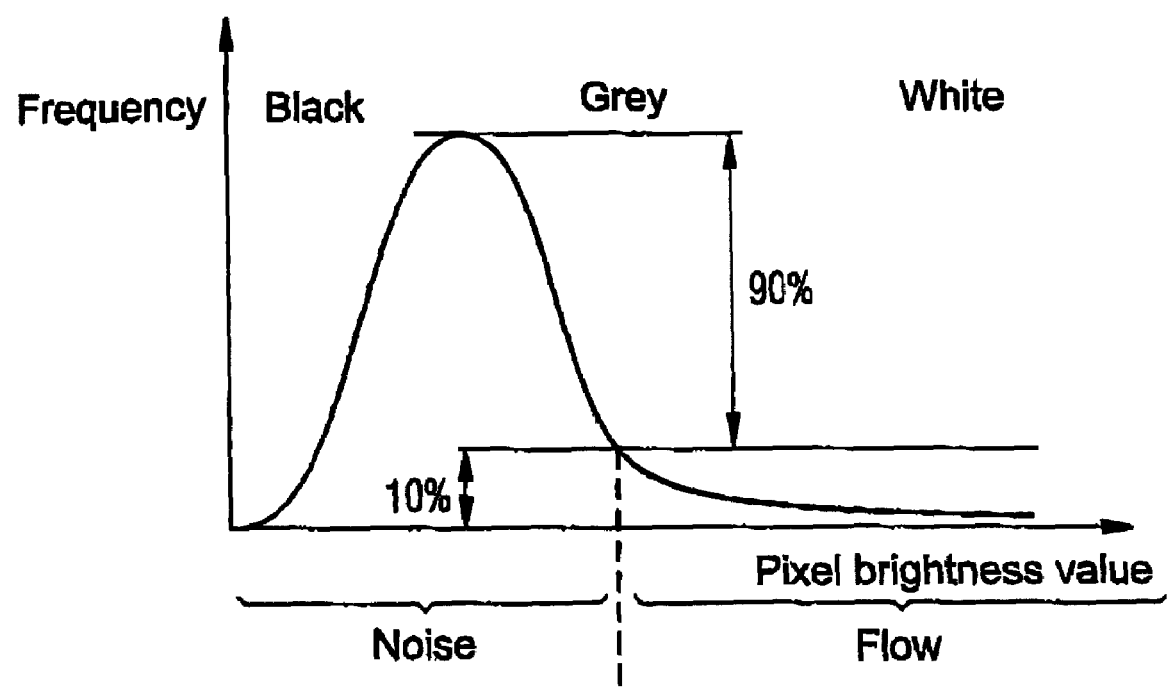
FIG. 4 shows a histogram based on an image of the magnitude image series to determine the threshold.
Figure 6A:
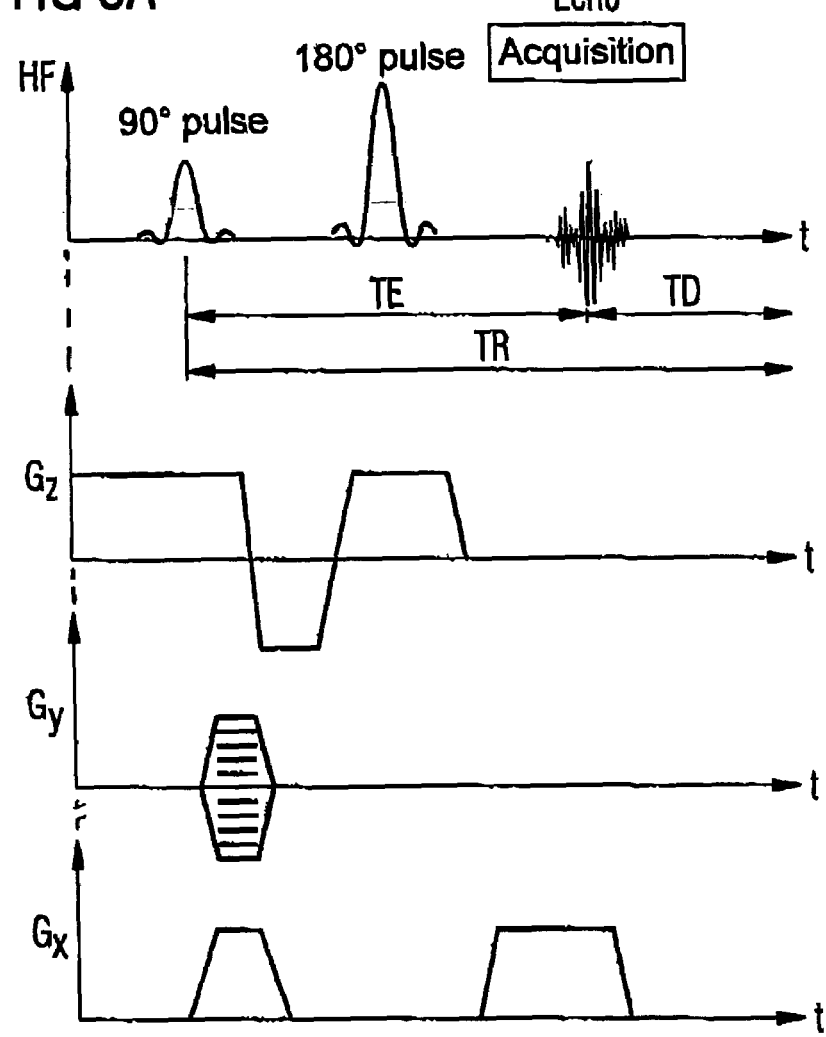
FIG. 6A schematically shows the time curve of the gradient pulse current functions of a spin-echo sequence.
Figure 6B:
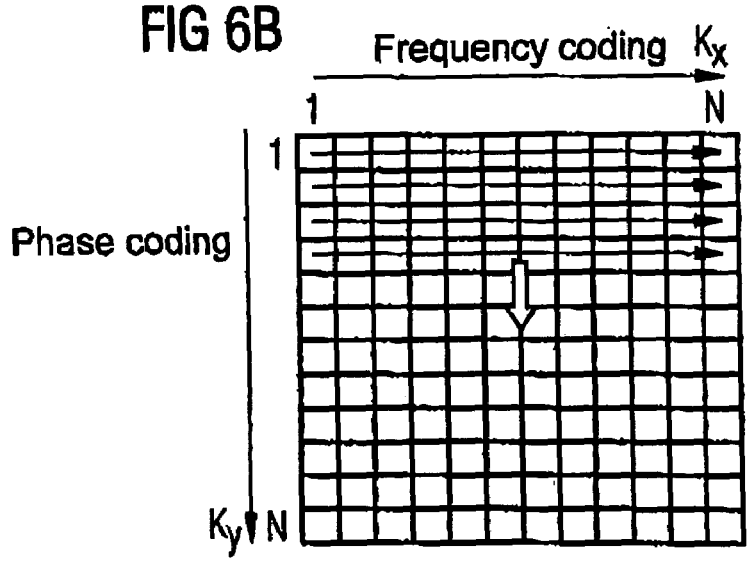
FIG. 6B schematically shows the temporal sampling of the k-matrix in a spin-echo sequence according to FIG. 6A.

Furthermore, it is also possible to segment the traversed regions in the magnitude image, or in the phase image on the basis of the magnitude image. For this, in a first step a histogram of the magnitude image is calculated Such a histogram is shown in FIG. 4.

The histogram is a Gaussian curve, with the peak representing the noise and the region to the right of this—thus the higher or, respectively, brighter pixel values beyond a threshold—represents the flow information. The threshold is established beforehand depending on the histogram, for example in the range of approximately 10% of the maximum of the curve. All pixels with values above the threshold are kept, all pixels with lower values are deleted, and the retention and deletion do not necessarily ensue in the magnitude image, but rather possibly ensue in the phase image. Alternatively, the brightness comparison can be implemented based on the average value of a (pixel) neighborhood (for example with eight neighbors) instead of on an individual pixel. In this manner, it is possible to create from magnitude image or from the phase image a mask according to FIG. 2D that exactly characterizes the blood-traversed regions.

The more precisely the cross-section or the geometry of the blood-traversed region is known, meaning the more exactly the segmentation ensues, the better the flow parameters (average velocity, flow rate, etc.) can be determined in the framework of a completely automatic calculation. It is therefore useful to also acquire from the anatomical image information in which, for example, the boundaries of the blood-traversed regions are determined by the vessel walls by means of a seed growth algorithm. Starting from a seed inside a traversed region, the existing flow regions are scanned from the inside out and the border is sought The sampling is based on a method for border detection, or on a method for edge detection. The designation of the seed ensues based on preceding segmentations, for example by determination of the focal point of a traversed region, thus ensuring that the seed is present inside the flow region. The seed growth algorithm can additionally be applied to the phase image and/or the magnitude image, such that further segmented data sets (for example again in the form of a mask) are produced and a qualitative selection can be made. Thus, for example, a confidence weighting can be used for evaluation of the segmentation of identical regions of the different three image types.

If one has decided on a segmented data set or a combination of the segmented data sets in the form of a mask or a filtered image, the segmented flow areas can undergo a calculation-based and therefore automatic subject analysis. The subject analysis includes, for example, consideration of the expansion and area of a traversed area, the shape and size or focal point, etc., on the basis of which characteristic flow parameters can be determined in combination with the phase image.

In the case of acquired image series, the segmentation does not have to ensue for each individual image. An image of the series is inventively, fully automatically segmented, and the segmented, traversed regions of this image are used as a starting region for (known) contour adaptation algorithms, or contour tracking algorithms, with an automatic segmenting automatically ensuing over the entire image series.

It is possible to automatically determine the velocity profile of a segmented, traversed region of a series, and on the basis of this to create a series-specific histogram, advantageously in a manner that corresponds to the standard of a Doppler ultrasound representation. Such a histogram is shown as an example in FIG. 5. It shows the velocity distribution of the blood flow in the aorta during a heart cycle (from systole to systole). The ordinate is divided into velocity intervals ($\Delta y_1$, $\Delta y_2$, $\Delta y_3$ etc.) that are respectively, time-dependently marked given occurrence of the corresponding velocity. Depending on the frequency of the existing velocity interval, the histogram is brightness-coded, such that, for example, a bright pixel represents a dominant velocity and a dark pixel in the histogram marks a velocity that occurs less often.

By means of the inventive method, a superimposition of the automatically segmented flow regions can ensue completely automatically with the anatomical image in an ultrasound color Doppler representation, which enables for the doctor a fast orientation of the flow relationships in the anatomy of the patient.

This type of representation (according to the ultrasound standard) is useful because the observer can assess the flow relationships faster and better from the color representation, and the doctor does not have to learn to read MR images, since he or she can resort to existing knowledge of ultrasound color Doppler flow measurement. The color-coding and a corresponding histogram representation (according to ultrasound standard) enable at a glance the flow direction (red/yellow for one flow direction, blue/turquoise for the opposite direction), the velocity of the flow (the brighter the faster) and the velocity distribution during a cycle (width of the histogram curve).

An inventive, automated velocity analysis over an entire image series enables the fast determination of the maximum occurring velocity value of thus series. This distinguished velocity value (also designated as "AUTOVENC"; standing for: auto velocity encoding) can be passed—but with a lower safety tolerance—to the protocol of a following (subsequent) new flow measurement. The velocity scales thus are optimally utilized, and aliasing effects in the phase image are prevented (aliasing effects are created when the maximum possible phase $\phi=180°$ is not associated with the maximum flow velocity but rather with a lower flow velocity).

Since the maximum flow velocities primarily lie in the middle of the traversed regions, an exact, clean border delimitation is not absolutely necessary for the determination of the AUTOVENC value. However, the elimination of pixels that are generated via noise is essential, because such pixel values lie at both ends of the velocity scale and thus can also simulate very high (maximum) velocities and therewith nonexistent AUTOVENC values, Theoretically, a single pixel that has not been filtered out by neighborhood analysis of the flow region is sufficient to determine an imaginary AUTOVENC value.

As already mentioned, the maximum expected velocity value (VENC value) adjustable by the user establishes the resolution of the velocity scale. In order in general to obtain a best possible resonance, in the framework of the present invention, it is possible to subsequently (automatically) define the measurement maximum velocity value (AUTOVENC value) as an upper limit of the (VENC) velocity scale, and thus to spread to measured scale over the adjusted (AUTOVENC) scale and to obtain a best-possible resolution in color Doppler representation.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for segmentation of fluid-traversed regions in a subject represented in a magnetic resonance tomography image in which fluid flows at velocity, comprising the steps of:
generating a phase image of an examination subject by acquiring, by magnetic resonance tomography data including velocity data, representing a fluid-traversed region of the subject and directionally-dependently encoding said velocity data; and
automatically segmenting said fluid traversed region in said phase image with no manual intervention; and
automatically evaluating said fluid traversed region in said phase image with no manual intervention.

2. A method as claimed in claim 1 wherein said phase image is comprised of pixels, and wherein the step of automatically segmenting said fluid-traversed region in said phase image comprises, for each pixel, automatically retaining or deleting that pixel dependent on a brightness comparison of that pixel with a neighbor pixel thereof.

3. A method as claimed in claim 1 wherein said phase image is comprised of pixels, and wherein the step of automatically segmenting said fluid-traversed region in said phase image comprises, for each pixel, automatically retaining or deleting that pixel dependent on a brightness comparison of that pixel with a defined number of neighbor pixels thereof.

4. A method as claimed in claim 3 comprising selecting said defined number of neighbor pixels independently of an environment of the pixel to be retained or deleted, by executing an algorithm in a computer.

5. A method as claimed in claim 3 comprising employing only pixels along at least one of eight primary directions, relative to the pixel to be retained or deleted, as said defined number of neighbor pixels.

6. A method as claimed in claim 5 comprising retaining or deleting each pixel dependent on a relationship of a brightness value difference, between the pixel to be retained or deleted and said defined number of neighbor pixels, to a defined threshold value.

7. A method as claimed in claim 6 comprising filtering said phase image dependent on an average value of said defined number of neighbor pixels.

8. A method as claimed in claim 1 comprising calculating a magnitude image based on said phase image, and segmenting said fluid traversed regions in said phase image using said magnitude image.

9. A method as claimed in claim 8 wherein said magnitude image is comprised of pixels, and wherein the step of segmenting said fluid traversed region in said phase image using said magnitude image comprises, for each pixel in said magnitude image, retaining or deleting that pixel dependent on a brightness value comparison of that pixel with a threshold value.

10. A method as claimed in claim 9 comprising deleting or retaining the pixel in the magnitude image.

11. A method as claimed in claim 9 wherein said phase image is comprised of pixels respectively corresponding to the pixels in the magnitude image, and comprising deleting the corresponding pixel in the phase image dependent on the brightness value comparison of the corresponding pixel in the magnitude image.

12. A method as claimed in claim 9 comprising determining an average brightness value of an environment of pixels for the pixel to be deleted or retained, dependent on a relationship of a difference between the brightness value of the pixel to be deleted or retained and said average value, with respect to said threshold value.

13. A method as claimed in claim 9 comprising dynamically selecting said threshold value.

14. A method as claimed in claim 9 comprising establishing said threshold value based on evaluation of a histogram of pixels in said magnitude image.

15. A method as claimed in claim 1 comprising simultaneously acquiring an anatomical image of the examination subject with said phase image, and wherein the step of automatically segmenting the fluid traversed region in said phase image comprises automatically segmenting the fluid traversed region in the phase image using said anatomical image.

16. A method as claimed in claim 15 wherein said anatomical image is comprised of pixels, and comprising segmenting said fluid traversed region in said phase image using a seed growth algorithm by identifying a pixel in the fluid traversed region in said anatomical image and sampling said pixel in said fluid traversed region from a border of said fluid traversed region.

17. A method as claimed in claim 16 comprising sampling said pixel inside said blood-traversed region using a sampling technique selected from the group consisting of border detection and edge detection.

18. A method as claimed in claim 1 comprising calculating a magnitude image from said phase image, said magnitude image being comprised of pixels, and comprising segmenting said fluid traversed region in said phase image using a seed growth algorithm by identifying a pixel in said fluid traversed region in said magnitude image and sampling said pixel in said fluid traversed region from a border of said blood-traversed region.

19. A method as claimed in claim 18 comprising sampling said pixel inside said blood-traversed region using a sampling technique selected from the group consisting of border detection and edge detection.

20. A method as claimed in claim 1 wherein said phase image is comprised of pixels, and comprising segmenting said fluid traversed region in said phase image using a seed growth algorithm by identifying a pixel in said fluid traversed region and sampling said pixel in said fluid traversed region from a border of said fluid traversed region.

21. A method as claimed in claim 20 comprising sampling said pixel inside said fluid traversed region using a sampling technique selected from the group consisting of border detection and edge detection.

22. A method as claimed in claim 21 wherein the step of automatically evaluating said fluid traversed region in said phase image comprises subjecting the segmented fluid traversed region to a subject analysis.

23. A method as claimed in claim 22 comprising in said subject analysis, analyzing at least one of an extent and area of said fluid traversed region, a shape of said fluid traversed region, a size of said blood-traversed region, and a focal point of said fluid traversed region.

24. A method as claimed in claim 1 comprising acquiring an anatomical image of the subject substantially simultaneously with said phase image, and generating a magnitude image from said phase image, and segmenting said fluid traversed region in each of said phase image, said anatomical image and said magnitude image, applying a confidence weighting to the segmented fluid traversed regions of the respective phase image, anatomical image and magnitude image, and using the segmented fluid traversed region having a highest confidence weighting.

25. A method as claimed in claim 1 comprising acquiring an image series, consisting of a plurality of phase images, of said subject by magnetic resonance tomography, and automatically segmenting the respective fluid traversed regions in each phase image in said series, and employing the respective fluid traversed regions of the phase images in the series in an algorithm selected from the group consisting of contour adaptation algorithms and contour tracking algorithms.

26. A method as claimed in claim 1 comprising acquiring an image series, consisting of a plurality of phase images, of said subject by magnetic resonance tomography, determining a velocity profile of blood in the respective fluid traversed regions of said phase images in said series, and generating a histogram for said series dependent on the respective velocity profiles.

27. A magnetic resonance tomography apparatus comprising:
   a magnetic resonance scanner that acquires data representing a fluid traversed region of an examination subject in which fluid flows at a velocity, said data including directionally encoded velocity data representing said fluid; and
   a computer supplied with said data that generates a phase image therefrom and that, with no manual intervention, automatically segments said fluid traversed region in said phase image and evaluates said fluid traversed region.

28. A computer software product loadable into a control and imaging computer of a magnetic resonance tomography apparatus, said computer program product causing said control and operating computer to:
   operate a magnetic resonance scanner to acquire data representing a fluid traversed region of an examination subject;
   generate a phase image from said data, including said directionally encoded velocity data;
   automatically segment, in said control and operating computer, said fluid traversed region in said phase image; and
   automatically evaluate said fluid traversed region in said phase image.

* * * * *